(12) United States Patent
Quibel et al.

(10) Patent No.: US 6,513,384 B1
(45) Date of Patent: Feb. 4, 2003

(54) METHOD AND APPARATUS FOR MEASURING THE LOAD BEARING CAPACITY OF A PLATFORM

(75) Inventors: Alain Quibel, Saint Etienne du Rouvray (FR); Michel Froumentin, Bois Guillaume (FR); Jacques Marignier, Mesnil-Esnard (FR); Maurice Leroy, Sotteville les Rouen (FR); Guy Morel, Caudebec les Elbeuf (FR)

(73) Assignee: Laboratoire Central des Ponts e Chaussees, Paris (FR)

( * ) Notice: Subject to any disclaimer, the term of this patent is extended or adjusted under 35 U.S.C. 154(b) by 0 days.

(21) Appl. No.: 09/830,001

(22) PCT Filed: Nov. 5, 1999

(86) PCT No.: PCT/FR99/02709

§ 371 (c)(1),
(2), (4) Date: Apr. 20, 2001

(87) PCT Pub. No.: WO00/28320

PCT Pub. Date: May 18, 2000

(30) Foreign Application Priority Data

Nov. 5, 1998 (FR) .......................................... 98 13922

(51) Int. Cl.[7] ................................................. G01N 3/30
(52) U.S. Cl. ........................... 73/594; 73/146; 73/636; 73/639
(58) Field of Search ............................ 73/594, 146, 8, 73/788, 790, 636, 639

(56) References Cited

U.S. PATENT DOCUMENTS

| | | | | |
|---|---|---|---|---|
| 3,427,877 A | | 2/1969 | Swift et al. ................... 73/146 |
| 4,174,636 A | * | 11/1979 | Pagano ........................ 73/636 |
| 4,409,823 A | * | 10/1983 | Gressin ....................... 73/146 |
| 4,958,306 A | * | 9/1990 | Powell et al. ................. 73/146 |
| 5,071,159 A | * | 12/1991 | Kamimura et al. ........... 280/707 |
| 5,571,961 A | * | 11/1996 | Gassner et al. ............... 73/146 |
| 5,659,140 A | * | 8/1997 | Jakob et al. .................. 73/788 |
| 5,723,768 A | * | 3/1998 | Ammon ......................... 73/8 |
| 6,161,429 A | * | 12/2000 | Marvel et al. ................ 73/146 |

FOREIGN PATENT DOCUMENTS

| | | |
|---|---|---|
| EP | 0 589 772 | 3/1994 |
| EP | 0 646 771 | 4/1995 |
| FR | 2 076 423 | 10/1971 |
| FR | 2 334 785 | 7/1977 |

* cited by examiner

Primary Examiner—Hezron Williams
Assistant Examiner—Jacques Saint-Surin
(74) Attorney, Agent, or Firm—Wolf, Greenfield & Sacks, P.C.

(57) ABSTRACT

The invention relates to a method and an apparatus for measuring the lift of a transport infrastructure road level and industrial floors. The apparatus comprises a wheel borne by a chassis pivotally mounted on a trailer towed by a vehicle. An unbalanced member causes the wheel to vibrate. The vertical acceleration of the chassis and of the wheel and the angle of the centrifugal force of the unbalanced member with the vertical, are continuously measured. The total force applied by the wheel, the chassis and the unbalanced member is calculated from the measurements of the accelerations, as is the deflection of the road level by double integration of the acceleration of the wheel.

9 Claims, 4 Drawing Sheets

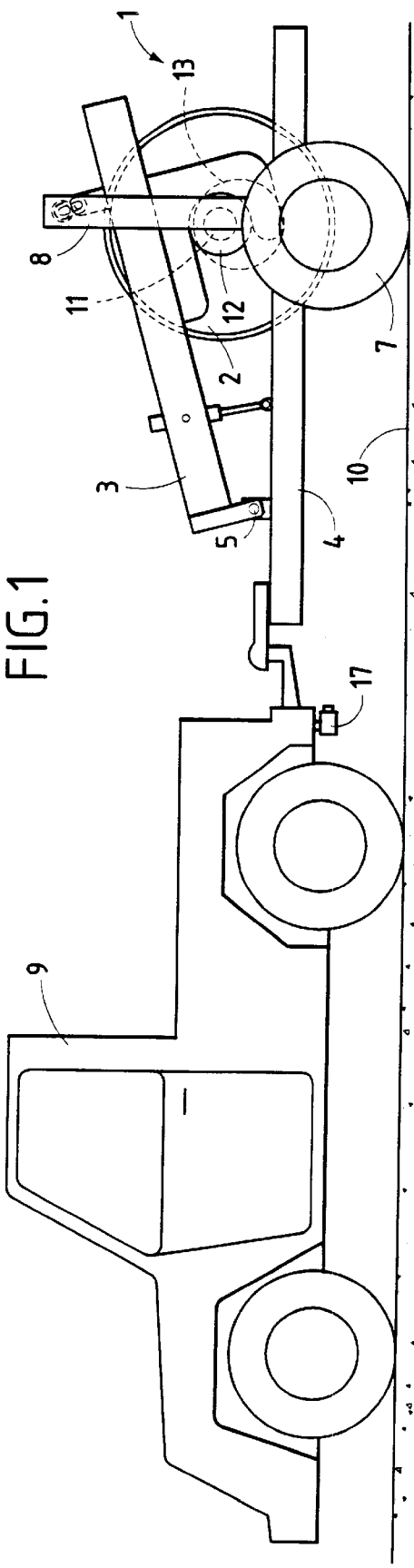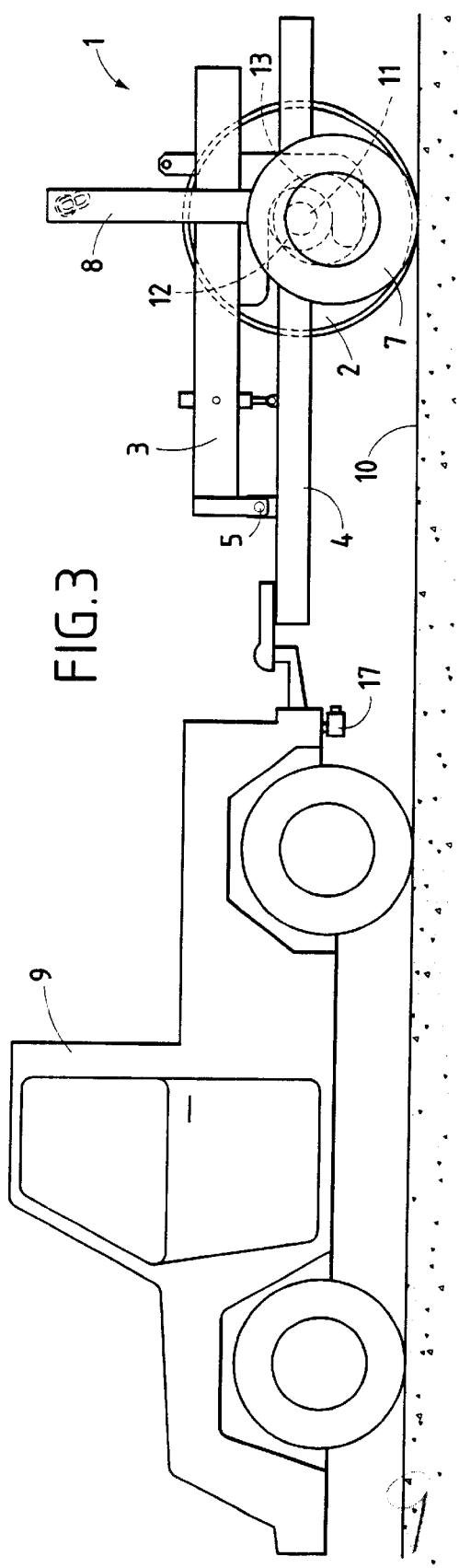

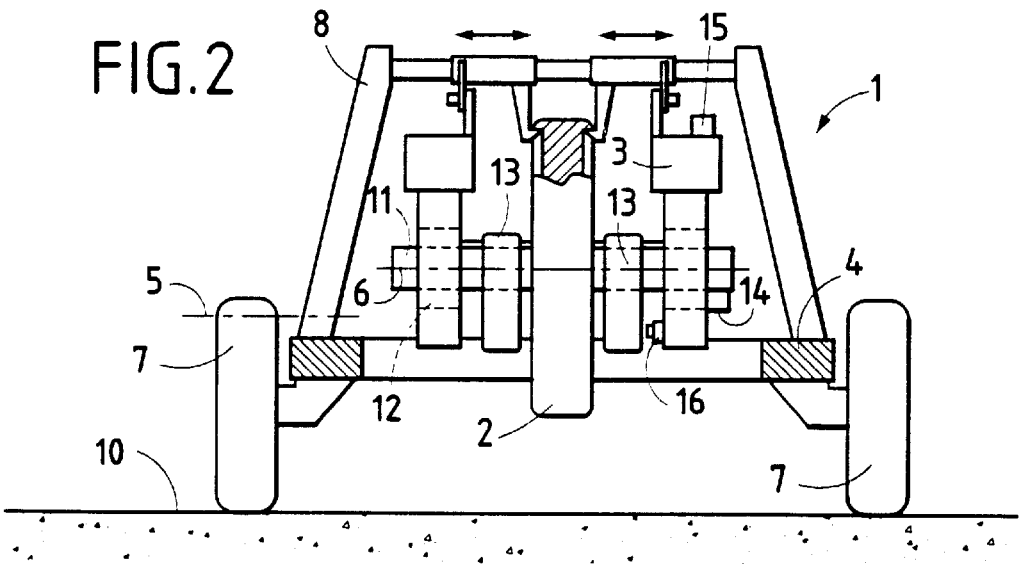
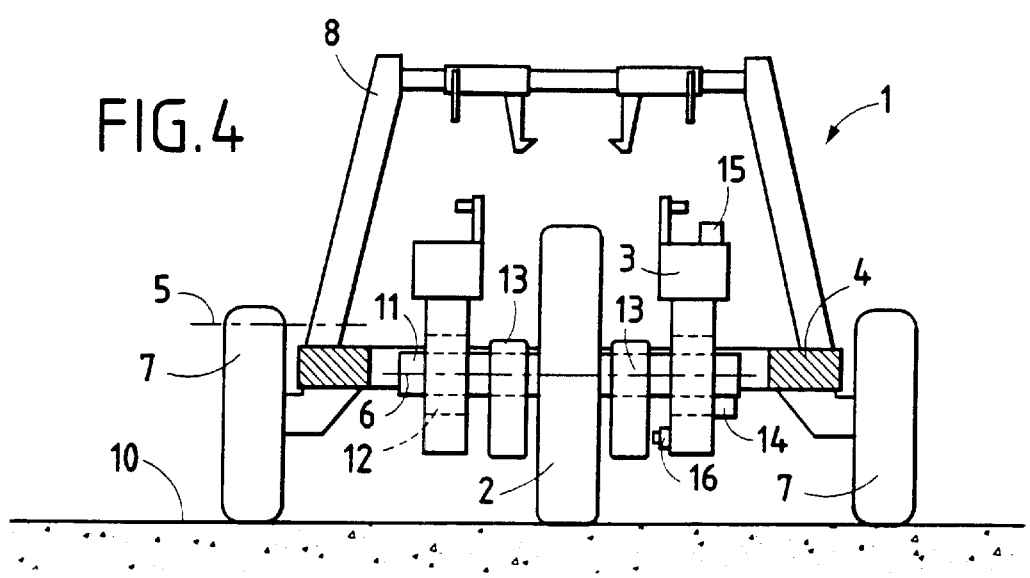

METHOD AND APPARATUS FOR MEASURING THE LOAD BEARING CAPACITY OF A PLATFORM

RELATED APPLICATIONS

Foreign priority benefits are claimed under 35 U.S.C. §119(a)–(d) or 35 U.S.C. §365(b) from French Application Number 98/13922, filed Nov. 5, 1998, and under 35 U.S.C. 365(a) from PCT International application PCT/FR99/02709, filed Nov. 5, 1999, which designated at least one country other than the United States. PCT application PCT/FR99/02709, of which this application is a national stage filing under 35 U.S.C. §371, was published under PCT Article 21(2) in French.

The present invention relates to a method for continuously measuring the stiffness or the elastic modulus of a transport infrastructure road level and industrial floors during works or in service, and to an apparatus for carrying out the method.

The method is applied to subgrades, levelling stones, or any other road level of which the desired modulus is included between 30 MPa and 300 MPa and which presents a satisfactory geometry for the circulation of the apparatus.

BACKGROUND OF THE INVENTION

At the present time, the lift of the levelling stones and subgrades is controlled by one of the following apparatus:
- plate bearing test truck
- dynaplate
- deflectograph.

The first two apparatus make a punctual measurement. In order to have an overall view of the homogeneity of the lift and the respect of the requirements, the controls should be carried out in accordance with a pre-established meshwork. The static plate bearing test is suitable for moduli of up to 200 MPa, but is relatively long.

The dynaplate is a shock apparatus in which the deformability of the subgrade sounded is assessed by the coefficient of restitution which represents the ratio between the heights of drop and rebound of a mass dropping on a series of springs arranged on a plate, having a diameter of 600 mm, placed on the ground. The dynaplate test is quicker than the static plate bearing test. Its sensitivity is maximum around 50 MPa, but becomes poor beyond 100 MPa due to the shape of the calibration curve between the elastic modulus and the coefficient of restitution, taking into account the choice of the characteristics of the apparatus.

The deflectograph delivers information on the deflection, generated by a rolling load, and which can be represented virtually continuously in longitudinal profile. By its design, it intervenes only on sites which are of easy access and where the flat and the deflection normally have favourable characteristics, such as on treated soils of small granulometry.

An improved version of dynaplate also exists, of which the dimensional characteristics are unchanged, but whose principle of measurement is different. In this improved version, the load plate comprises a load cell allowing access to the acquisition of the force F transmitted to the ground as a function of time upon impact, as well as a sensor of vertical displacement during the shock. The combination of these two data gives the effort/deformation curve and allows access to the value of the modulus. This method exploits the ascending branch of the force/deflection curve obtained during a cycle of impact, and it furnishes a more substantial measurement than that obtained by the traditional dynaplate, up to a level of modulus of the order of 200 MPa. However, the measurement remains punctual.

SUMMARY OF THE INVENTION

Starting from this state of the art, the invention has for its object to propose a method for continuously measuring the stiffness or elastic modulus of the road level.

The present invention attains its object in that the proposed method comprises the following steps of:
- rolling on the road level a wheel of mass Mr suspended beneath a chassis of mass Mc,
- subjecting the wheel to vertical vibrations by means of an unbalanced member rotating about the axis of the wheel and subjected to a centrifugal force Fc,
- measuring as a function of time the vertical acceleration Gr of the wheel and the vertical acceleration Gc of the chassis by means of acceleration sensors mounted on the wheel and on the chassis,
- measuring as a function of time the angular phase $\phi$ between the direction of the centrifugal force Fc of the unbalanced member and the vertical by means of a sensor,
- calculating as a function of time the vertical component FTA of the force applied by the wheel on the road level,
- calculating as a function of time the vertical deformation d undergone by the road level from the measurement of the vertical acceleration Gr of the wheel,
- establishing for each cycle of vibration the loop of the vertical component FTA with respect to the deformation d,
- calculating at each cycle of vibration the gradient of the loop in the branch of the ascending vertical components in order to obtain the stiffness of the road level.

The following arrangements are also advantageously adopted:
- the gradient of the curve is calculated in the range of ascending vertical components included between 30% and 90% of the maximum vertical component;
- the elastic modulus is calculated by multiplying the value of the stiffness by a coefficient of calibration C determined by prior experimentation;
- the frequency of the vibrations of the wheel is included between 20 and 50 HZ;
- the wheel is advanced at a speed close to 1 m/sec.;
- the speed of displacement of the wheel is continuously measured;
- the average stiffness of the road level per unit of distance covered is calculated by calculating the average of the stiffnesses calculated during the cycles of vibrations corresponding to this unit of distance covered;
- the average stiffnesses calculated as a function of the distance are continuously displayed on a display screen.

The invention also relates to an apparatus for carrying out the method according to the invention.

This apparatus is characterized in that it comprises:
- a towable trailer resting on wheels for rolling over the ground,
- a chassis of mass Mc mounted on the trailer so as to be able to pivot about a transverse axle,
- a wheel of mass Mr equipped with an unbalanced member and suspended beneath the chassis, means for rotating the unbalanced member, a first acceleration sensor mounted on the chassis, a second acceleration sensor mounted on the wheel, a sensor detecting the angle of the unbalanced member, means for calculating, as a function of time, the component of the force applied by the wheel on the road level, means for calculating, as a function of time, the vertical deformation undergone by the road level, means for establishing, upon each cycle of vibration, the vertical component with respect to the deformation, and means for calculating the stiffness of the road level upon each cycle of vibration.

The invention will be more readily understood on reading the following description given by way of example and with reference to the accompanying drawings in which:

BRIEF DESCRIPTION OF THE DRAWINGS

FIG. 1 is a side view of the apparatus according to the invention in roadway condition.

FIG. 2 is a rear view of the apparatus of FIG. 1, in partial section.

FIG. 3 is a side view of the apparatus according to the invention in operating condition.

FIG. 4 is a rear view of the apparatus of FIG. 3 in operating condition.

DETAILED DESCRIPTION OF THE DRAWINGS

Figure 5:
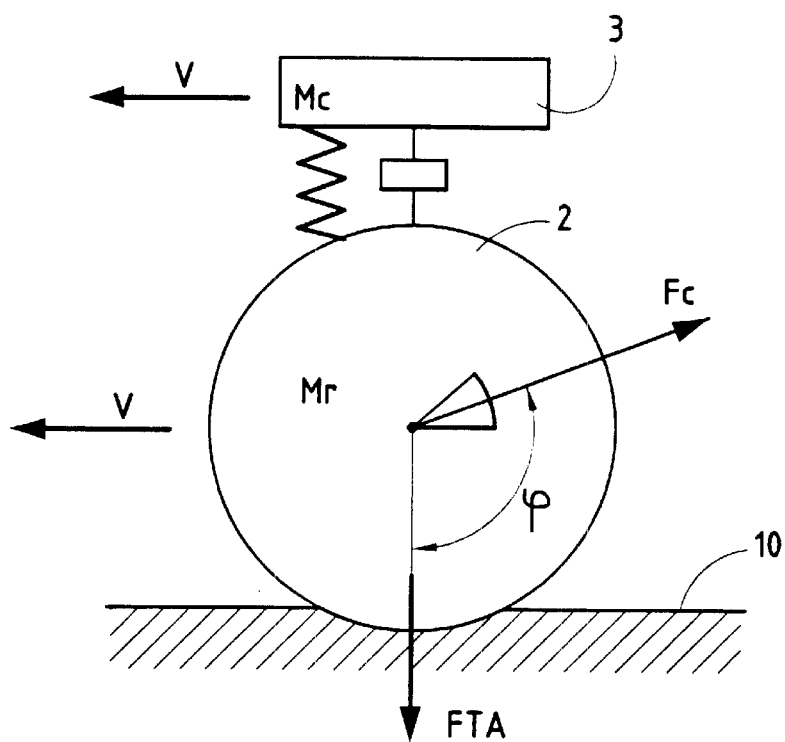
FIG. 5 schematically shows the wheel and the chassis in operating condition.

Referring now to the drawings, FIGS. 1 to 4 firstly show an apparatus 1 intended for continuously measuring the stiffness and the elastic modulus of a transport infrastructure road level and industrial floors during works or in service. The apparatus essentially comprises a wheel 2 of mass Mr suspended beneath a chassis 3 of mass Mc. The chassis 3 is mounted on a trailer 4 so as to be able to rotate freely about a horizontal and transverse axle 5 parallel to axle 6 of the wheel 2. The trailer 4 comprises two wheels 7 for rolling over the ground and a frame 8 which serves to maintain the wheel 2 and the chassis 3 in a raised position, as shown in FIGS. 1 and 2, during transport of the apparatus 1 from one worksite to another. The trailer 4 is towed by a vehicle 9 during its displacement on the highway and likewise when used on a worksite.

FIGS. 3 and 4 show the apparatus 1 during use on a worksite. In this situation, the wheel 2 and the chassis 3 are disconnected from the frame 8. The wheel 2 then rests on the road level 10 of which it is desired to measure the stiffness and elastic modulus, and rolls freely when the trailer 4 towed by the vehicle 9 advances.

The axle 5 of the chassis 3 is preferably located at the front of the trailer 4 and is remote from the axle 6 of the wheel 2, the latter being located to the rear of the chassis 3.

When the apparatus 1 is in work position, the role of the trailer 4 is to tow the chassis 3 and the wheel 2 and to maintain the wheel 2 in a substantially vertical plane parallel to the direction of advance of the vehicle 9.

The wheel 2 comprises a horizontal shaft 11 mounted on the chassis 3 via bearings 12 which allow relative vertical displacements between the wheel 2 and the chassis 3.

The horizontal shaft 11 of the wheel 2 is equipped with synchronized unbalanced members 13 which are driven in rotation about the axis 6 at a constant speed included between 20 and 50 revs per second, by means of a preferably hydraulic motor. The energy necessary for driving this motor is supplied by the vehicle 9 in order that the mass of the apparatus 1 be constant for the duration of the measurement.

The unbalanced members 13 are subjected to a centrifugal force Fc which is a function of the moment of eccentricity of the unbalanced members 13 and their speed of rotation.

The wheel 2 and the chassis 3 are then subjected to vertical vibrations at a frequency included between 20 and 50 Hz depending on the speed of rotation of the unbalanced members.

FIG. 5 schematically shows the vertical component, called total applied force FTA, of the forces applied by the wheel 2, the chassis 3 and the unbalanced members 13 on the road level 10.

This vertical component FTA is the sum of the following forces:

the weight of the wheel 2 and of the chassis 3, or $(Mr+Mc) \times g$, g being the earth's attraction, the force of inertia of the wheel 2, viz. $Mr \times Gr$, Gr being the vertical component of the acceleration of the wheel 2, the force of inertia of the chassis 3, viz. $Mc \times Gc$, Gc being the vertical component of the acceleration of the chassis 3, and the vertical component of the centrifugal force Fc of the unbalanced members 13, viz. $Fc \times \cos \phi$, $\phi$ being the phase shift between the direction of the centrifugal force Fc and the vertical.

We therefore have the equation:

$$FTA=(Mr+Mc) \times g+Mr \times Gr+Mc \times Gc+Fc \times \cos\phi$$

The masses Mr and Mc are measurable constants and the centrifugal force Fc is constant since the speed of rotation of the unbalanced members is constant.

Measurement of the accelerations Gr and Gc and measurement of the angle $\phi$ as a function of time therefore make it possible to calculate, as a function of time, the force FTA applied by the wheel 2 on the road level 10.

According to the present invention, the wheel 2 is equipped with an accelerometer 14 of the piezo-electric type and the chassis 3 is likewise equipped with an accelerometer 15 of piezo-electric type.

The angle $\phi$ is calculated as a function of time thanks to an optical sensor 16 which delivers a pulse every time the unbalanced members 13 pass through bottom.

The value furnished by the accelerometer 14 which measures the vertical acceleration of the wheel 2 is used for calculating the vertical amplitude of vibration by double integration.

This integration may be effected after factorization into Fourier series of the acceleration signal Gr and double integration of the terms of the series.

The vertical amplitude of vibration corresponds to the vertical deformation d or deflection undergone by the road level 10 at the moment of the impact.

Figure 6:
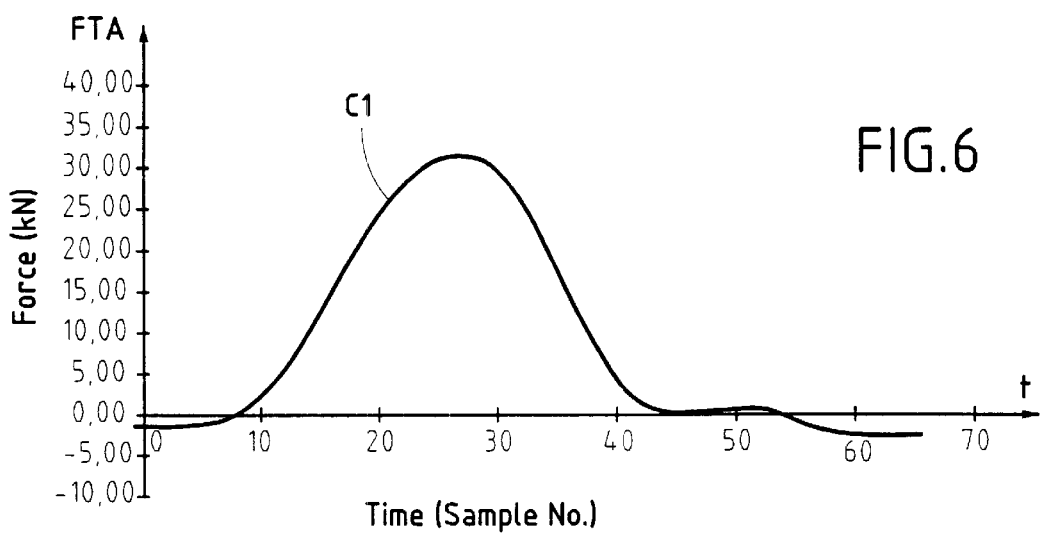
FIG. 6 shows the curve representative of the total force applied during a period or an average of 20 periods.
Figure 7:
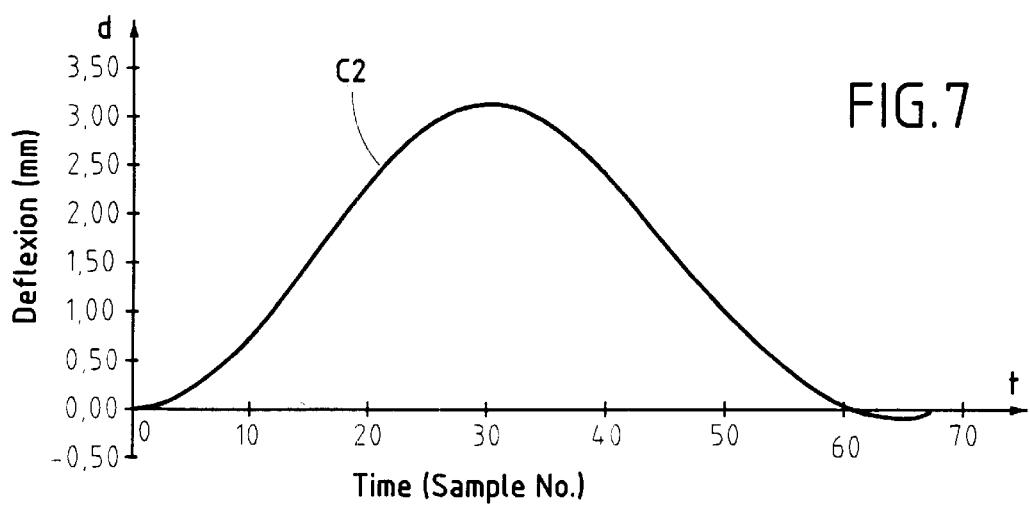
FIG. 7 shows the curve representative of the deflection in the course of a period.
Figure 8:
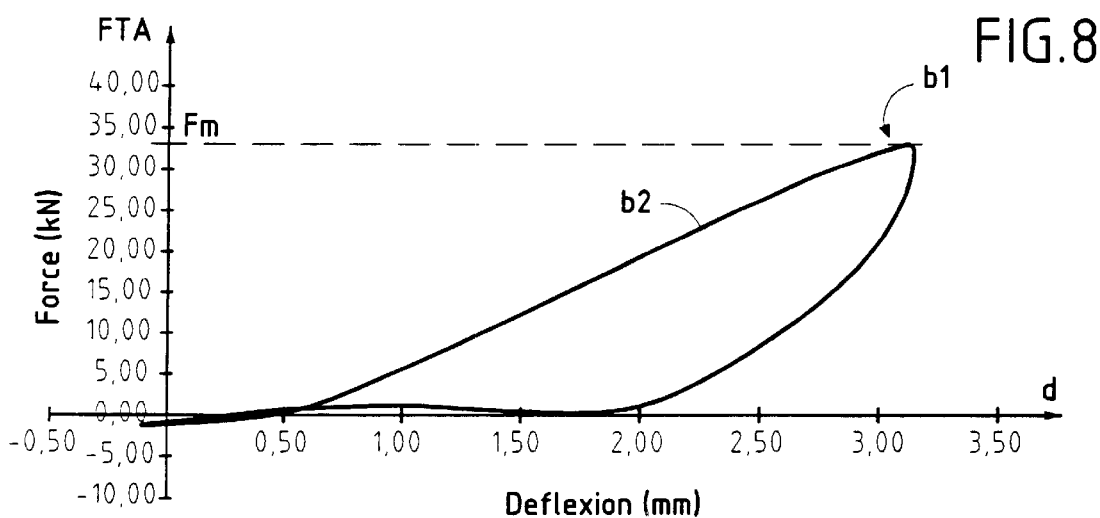
FIG. 8 shows the force/deflection loop.

FIG. 6 shows the curve (C1) of variation of the force FTA as a function of time t for a cycle of vibration, and FIG. 7 shows the curve (C2) of the variation of the deflection d of the road level 10 as a function of time t for the same cycle of variation. FIG. 8 shows the loop (b1) representative of the variation of the force FTA as a function of the deflection d of the road level 12. This loop (b1) comprises an upper branch (b2) which corresponds to the ascending vertical components.

This branch (b2) presents a substantially rectilinear portion whose gradient gives the measurement of the stiffness of the road level 10.

In practice, the gradient is measured over the portion of the upper branch (b2) included between 30% and 90% of the maximum force Fm measured.

The vehicle 9 is also equipped at the rear with a Doppler radar 17 which makes it possible to measure the speed of the vehicle 9 and thereby the distance covered by the wheel 2.

The accelerometers 14 and 15 are connected to a central unit 18 borne by the vehicle 9 via an analog data acquisition card 19. The optical sensor 16 and the Doppler radar 17 are also connected to the central unit 18 and the latter communicates with a micro-computer 20 located in the driver's cabin of the vehicle 9.

Figure 9:
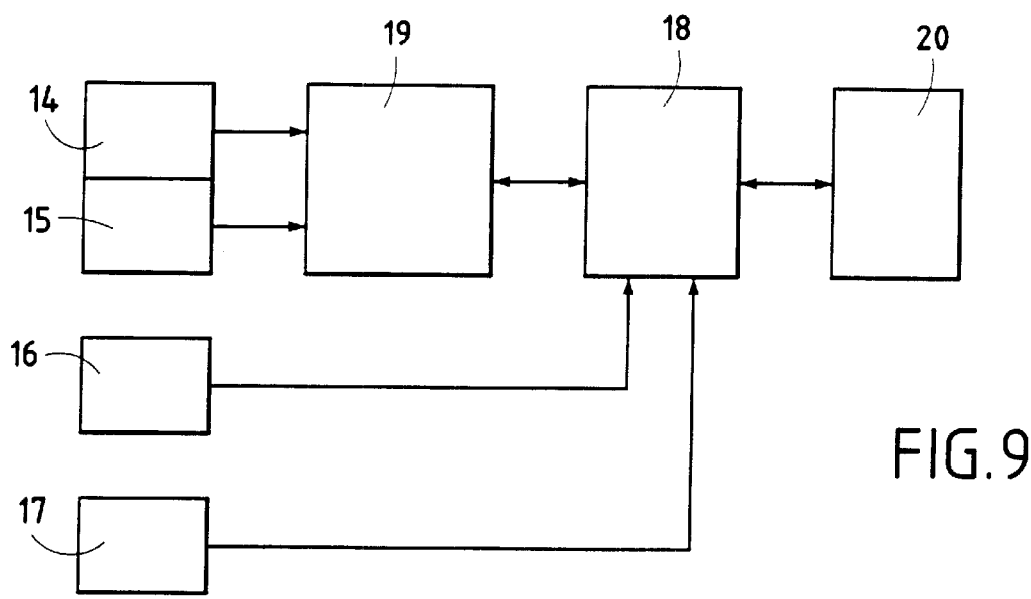
FIG. 9 shows the architecture of the data acquisition and calculating system.

FIG. 9 shows the architecture of the ensemble, made to operate in real time by a VME system built around a microprocessor 68020 for example and a real time core P SOS.

The core manages the tasks of acquisition, synchronization, processing, transfer and dialogue with the micro-computer 20, as well as the control of the ensemble.

The acquisition and sampling process is synchronized on the basis of the information on the revolutions of unbalanced members furnished by the optical sensor 16, which triggers off a series of measurements, by samplings covering 20 successive periods. A single period from the average of these 20 periods is produced in real time during the acquisition task. The processing task consists in making all the calculations resulting in the value of the rigidity of the road level 10. The useful data are then transferred to the micro-computer 20. These data include the registration number, the frequency of vibration, the speed of translation, the cumulated distance, the calculated rigidity, the maximum total force Fm applied and the amplitude of the vibration.

Right from the beginning of the processing, a new sequence of acquisition is launched. The number of 20 periods results from the desire to express the lift in elementary zones of more than one meter and from the necessity of the acquisition time to be at least equal to the sum of the processing and transfer times in order not to lose the acquisition information.

From the signals sampled, the processing consists, by addition of the forces, in determining the total applied force FTA which is smoothed by a Fourier factorization of order 5, and in proceeding with the double integration of Gr by Fourier series to order 10 in order to rise to the value of the deflection d. The two values FTA and d are brought together in a graph (cf FIG. 8) which shows that, by suitably parametering the bounds (example: lower bound 30% of Me and upper bound 90% of Fm), the processing by regression of the useful part (b2) of the curve (b1) furnishes the value of the rigidity of the road level allocatable to the zone sounded during the 20 periods. It should be noted that 20 periods of vibrations at a frequency of 35 Hz corresponds to a duration of 0.57 seconds, during which the advance of the apparatus 1 is of the order of 0.50 m at the speed of 1 m/sec. It should also be noted that the sampling frequency of 2 KHz makes it possible to obtain 57 points per period at 35 Hz.

By displaying the rigidity, calculated as a function of the distance covered, on a screen connected to the microprocessor 20, the operator or driver of the vehicle 9 can visualize the curve of the rigidity as a function of the distance covered, in the form of a graph.

By way of information, the mass Mr of the wheel 2 is 600 kg, the mass Mc of the chassis 3 is 400 kg, the diameter of the wheel 2 is 1 m, and the width of the wheel 2 is 0.10 m.

A coefficient of calibration C, determined from prior experimentation of the apparatus 1 with respect to methods in force for measuring the elastic modulus of road levels, makes it possible to obtain measurement of the elastic modulus of the road level 10 sounded from the stiffness measured by the apparatus 1. The coefficient of calibration C is a constant of the apparatus 1 and corresponds to a fixed choice of characteristics of concept of the apparatus, for example its amplitude of vibration, and of functioning, for example the speed.

From the practical point of view, the unbalanced members 13 may take two values, depending on the direction of rotation applied.

The apparatus 1 is capable of functioning with a low amplitude, in which case the direction of rotation of the unbalanced members 13 is opposite the direction of rotation of the wheel 2 during advance of the apparatus 1. This adjustment corresponds to the usual case of sounding of road levels 10 between 30 and 300 MPa.

It is also capable of functioning with a high amplitude, in which case the direction of rotation of the unbalanced members 13 is the same as that of the wheel 2. This adjustment is only valid with road levels 10 having moduli less than 80 MPa and increases the precision of the measurement in the range 30-60 MPa in particular. Beyond 80 MPa, lift-offs of the wheel 2 would no longer enable the signals to be correctly processed.

The moment of eccentricity of the unbalanced members is 0.3 mkg for a low amplitude of vibration and 0.6 mkg for a high amplitude.

The conditions of use of the apparatus 1 are the usual conditions of tests for measuring lift of road levels, i.e. the road level 10 must not include any frozen portion.

The apparatus 1 is capable of making measurements in longitudinal gradient up to 7% and in transverse gradient up to 5%. Outside these conditions, the measurements effected may present a slight bias.

It is unnecessary to effect a pre-passage of any equipment on the road level 10. Respect of the non-skidding conditions of the road levels 10 admitted by the rules of the art normally satisfies the trafficability of the vehicle 9/trailer 4 assembly in the domain mentioned above.

What is claimed is:

1. Method for continuously measuring the stiffness of a transport infrastructure road level and industrial floors, wherein it comprises the following steps of:

rolling on the road level a wheel of mass Mr suspended beneath a chassis of mass Mc, subjecting the wheel to vertical vibrations by means of an unbalanced member rotating about the axis of the wheel and subjected to a centrifugal force Fc, measuring as a function of time the vertical acceleration Gr of the wheel and the vertical acceleration Gc of the chassis by means of acceleration sensors mounted on the wheel and on the chassis, measuring as a function of time the angular phase φ between the direction of the centrifugal force Fc of the unbalanced member and the vertical by means of a sensor, calculating as a function of time the vertical component FTA of the force applied by the wheel on the road level, calculating as a function of time the vertical deformation d undergone by the road level from the measurement of the vertical acceleration Gr of the wheel, establishing for each cycle of vibration the loop of the vertical component FTA with respect to the deformation d, calculating at each cycle of vibration the gradient of the loop in the branch of the ascending vertical components in order to obtain the stiffness of the road level.

2. The method of claim 1, wherein the gradient of the loop is calculated in the range of ascending vertical components included between 30% and 90% of the maximum vertical component.

3. The method of claim 1, wherein the elastic modulus of the road level is calculated by multiplying the value of the stiffness by a coefficient of calibration C determined by prior experimentation.

4. The method of claim 1, wherein the frequency of the vibrations is included between 20 and 50 HZ.

5. The method of claim 1, wherein the wheel is advanced at a speed close to 1 m/sec.

6. The method of claim 1, wherein the speed of displacement of the wheel is measured continuously.

7. The method of claim 1, wherein the average stiffness of the road level per unit of distance covered is calculated by calculating the average of the stiffnesses calculated for the cycles of vibrations corresponding to this unit of distance covered.

8. The method of claim 7, wherein the average stiffnesses calculated as a function of the distance are continuously displayed on a display screen.

9. Apparatus for carrying out the method of claim 1, wherein it comprises:

a towable trailer resting on wheels for rolling over the ground, a chassis of mass Mc mounted on the trailer so as to be able to pivot about a transverse axle, a wheel of mass Mr equipped with an unbalanced member and suspended beneath the chassis, means for rotating the unbalanced member, a first acceleration sensor mounted on the chassis, a second acceleration sensor mounted on the wheel, a sensor detecting the angle of the unbalanced member, means for calculating the vertical deformation undergone by the road level, as a function of time, means for establishing, upon each cycle of vibration, the loop of the vertical component with respect to the deformation, and means for calculating the stiffness of the road level upon each cycle of vibration.

* * * * *